United States Patent [19]

Zook

[11] Patent Number: 5,181,914
[45] Date of Patent: Jan. 26, 1993

[54] MEDICATING DEVICE FOR NAILS AND ADJACENT TISSUE

[76] Inventor: Gerald P. Zook, 9708 Woodlawn Ave. N., Seattle, Wash. 98103

[21] Appl. No.: 879,792

[22] Filed: May 6, 1992

Related U.S. Application Data

[63] Continuation-in-part of Ser. No. 395,186, Aug. 18, 1989, abandoned, which is a continuation-in-part of Ser. No. 234,585, Aug. 22, 1988, abandoned.

[51] Int. Cl.⁵ ............................................. A61F 13/02
[52] U.S. Cl. ................... 604/307; 604/304; 604/292; 128/888; 128/893
[58] Field of Search ............... 128/846, 888, 893, 894; 604/292, 304, 307; 2/21

[56] References Cited

U.S. PATENT DOCUMENTS

| | | | |
|---|---|---|---|
| 2,847,005 | 8/1958 | Bourne | 602/58 |
| 3,419,006 | 12/1968 | King | 602/48 |
| 3,814,095 | 6/1974 | Lubens | 604/307 |
| 4,158,359 | 6/1979 | Kurokawa et al. | 128/630 |
| 4,379,454 | 4/1983 | Campbell et al. | 604/897 |
| 4,631,227 | 12/1986 | Nakamura | 604/289 |
| 4,788,971 | 12/1988 | Quisno | 604/289 |
| 4,842,931 | 6/1989 | Zook | 428/354 |
| 5,015,228 | 5/1991 | Columbus et al. | 604/307 |
| 5,098,421 | 3/1992 | Zook | 604/367 |

Primary Examiner—Paul Prebilic
Attorney, Agent, or Firm—John F. Ingman

[57] ABSTRACT

A medicating device for human nails and adjacent tissue which, in the preferred embodiment, includes a transparent viscoelastic gel pad having one or more pharmacologically-active substances incorporated therein; a sheet of transparent, impermeable, and elastic material providing an occlusive layer adjacent to the upper surface of the viscoelastic gel pad; an elastic retaining ring perimetrically surrounding the viscoelastic gel pad to prevent migration due to shoe pressure; and a porous meshwork attached to the elastic retaining ring so as to additionally anchor the gel pad from migration. The porous meshwork member may be located at the surface of the viscoelastic gel pad opposite the occlusive covering sheet, or may run through the viscoelastic gel pad in its anchoring function. The viscoelastic gel pad, occlusive covering sheet, and elastic retaining ring with porous meshwork may be secured to the digit of the wearer by a transparent digit-engaging elastic tubular sheath, or by an adhesive tape bandage with a visual access opening.

10 Claims, 2 Drawing Sheets

U.S. Patent     Jan. 26, 1993     Sheet 1 of 2     5,181,914
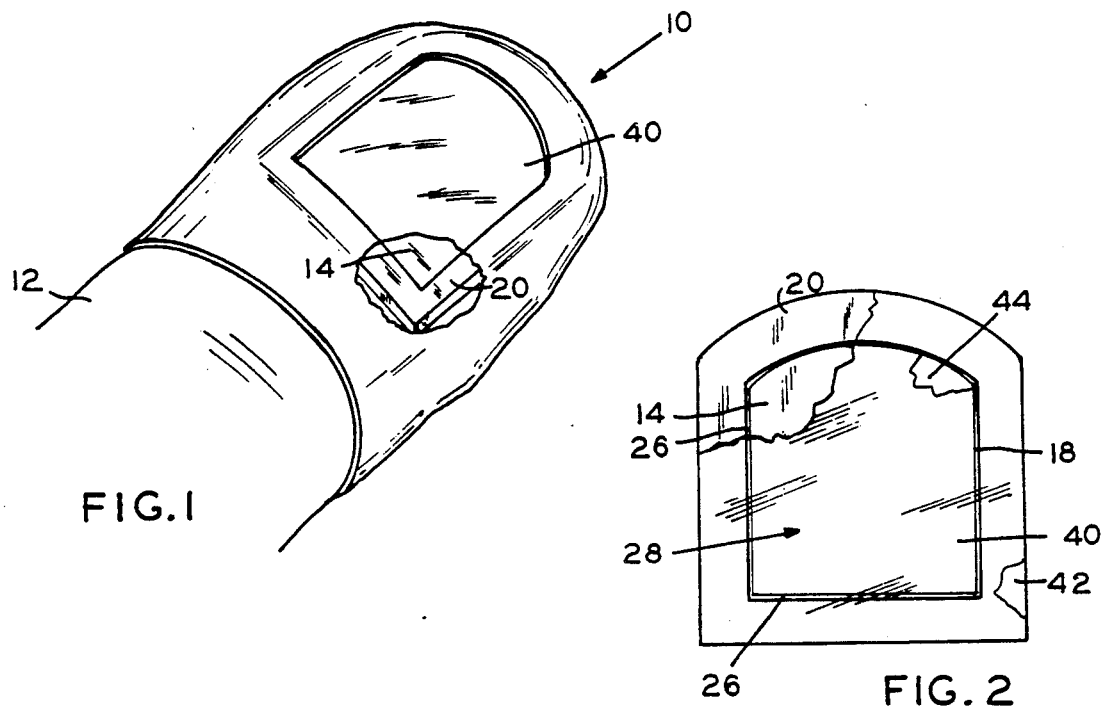
FIG. 1
FIG. 2
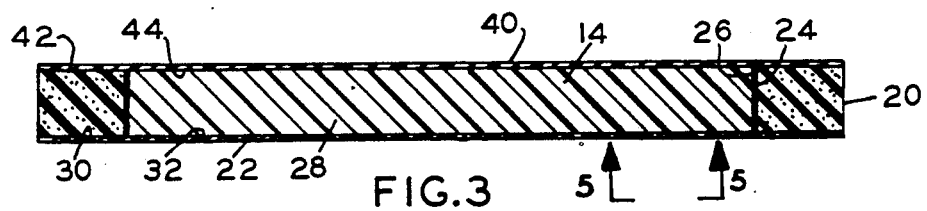
FIG. 3
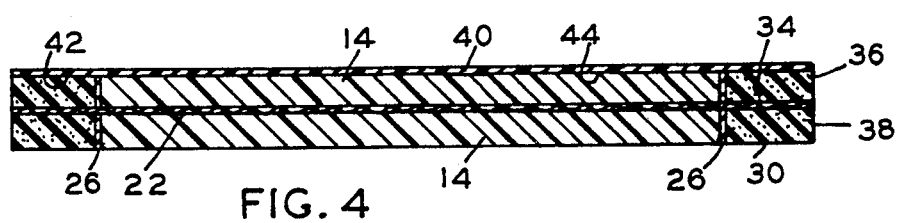
FIG. 4
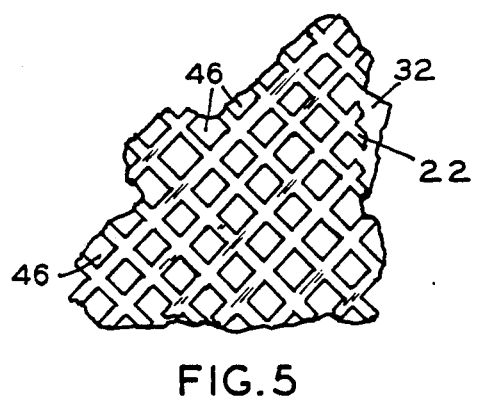
FIG. 5

MEDICATING DEVICE FOR NAILS AND ADJACENT TISSUE

This is a continuation-in-part of co-pending application Ser. No. 07/395,186, filed Aug. 18, 1989 now abandoned, which in turn is a continuation-in-part of Ser. No. 07/234,585, filed Aug. 22, 1988, now abandoned.

BACKGROUND OF THE INVENTION

1. Field of the Invention

This invention relates to the general field of medicating devices for human nails and adjacent tissue and, more particularly, a medicating device utilizing a viscoelastic gel pad which is supported by a perimetric elastic retaining ring and a porous meshwork attached to the elastic retaining ring.

2. Description of the Prior Art

Historically there have been many different ways of delivering medication to human nails and adjoining tissue. By far the most commonly employed means have been topically applied formulations such as creams, ointments, tinctures, aqueous solutions, and the like. Unfortunately, when these types of formulations are applied to pedal lesions, the medication is quickly absorbed or rubbed off by socks or shoes. For example, the treatment of mycotic (fungally infected) toenails by the application of antifungal creams or ointments is generally an exercise in futility, because the medication will not remain on the nail once socks or shoes are applied. One method of treating mycotic toenails involves constructing a medication reservoir with an occlusive dressing such as plastic tape or latex from a surgeon's glove. This technique, and even "simplified" versions of it, are very awkward and time consuming. I previously addressed this problem by designing a toenail medicating bandage which incorporated a medication reservoir to hold a urea ointment or other pharmacologically active agent. That toenail medicating bandage comprised an "adhesive seal" one or two millimeters thick which encircled the diseased nail, and a flexible, stretchable, waterproof diaphragm connected to the upper circumference of the adhesive seal such that a sealed-in medication reservoir was formed. The reservoir was to be filled with a medicinal ointment, cream, jelly, or similar drug vehicle and incorporated into a flexible, waterproof, digital bandage. When applied to the digit, the adhesive seal was designed to prevent medication from being squeezed out of the drug reservoir through a cleft in the adhesive seal/tissue interface. During the field trials of that particular medicating bandage, it was discovered that the extreme pressure generated within the medication reservoir by shoes exceeded the adhesive capabilities of commonly employed medical adhesives, and that the ointment, cream, or jelly would inevitably be squeezed through a failure in the adhesive seal/tissue interface and leak out of the medication reservoir. Stronger adhesives were contemplated but not employed due to the danger of damaging tissue. This problem was partially resolved when 1 inserted a pad of the viscoelastic hydrophilic gel, as described by King in U.S. Pat. No. 3,419,006, into the medication reservoir. During field trials of this medicating bandage, I discovered that the gel pad resisted being squeezed out of the medication reservoir and, in subsequent development utilizing a perimetric elastic retaining ring with an attached porous meshwork, the resulting medication-supplying unit was of sufficient strength that the adhesive means of the seal could be eliminated altogether. This development, of course, meant that the danger of tearing or avulsing soft tissue when removing the medication device was greatly reduced. This also meant that a sealed-in medication reservoir was no longer required to perform the intended function, which resulted in a highly simplified medicator for diseased human nails which takes advantage of the structural strength of viscoelastic gels when contained within a perimetric retaining ring and additionally supported by an attached porous meshwork.

SUMMARY OF THE INVENTION

Accordingly, it is an object of the present invention to provide a medicating device for human nails and adjacent tissue which is able to occlusively cover and hydrate the target lesions allowing for better diffusion of the medication.

It is a further object of the present invention to provide a medicating and padding device for human nails and adjacent tissue incorporating a viscoelastic gel pad which will conform to the shape of the target lesion, resulting in maximization of the surface area of contact between the gel pad and the target lesion, and furthermore will dissipate externally-applied pressure or frictional forces in a superior manner.

It is a further object of the present invention to provide a pedal drug delivery system that will allow medication to be delivered to the target lesion rather than being absorbed or rubbed off by socks or shoes.

It is a further object of the present invention to provide a padding and medicating device for the foot incorporating a viscoelastic gel pad which is prevented from migrating away from its intended site of application when worn inside a shoe by providing a supporting structure that prevents gel migration.

Yet another object of the present invention is to provide a medicating and padding device that utilizes a transparent gel, a transparent occlusive covering, and a porous meshwork, which allow the target lesion to be visualized through the transparent device for accurate placement of the device and monitoring of the target lesion during the course of therapy.

The invention, in the preferred embodiment, includes a transparent viscoelastic gel pad having one or more pharmacologically-active substances incorporated therein; a sheet of transparent, impermeable, and elastic material providing an occlusive layer adjacent to the upper surface of the viscoelastic gel pad; an elastic retaining ring perimetrically surrounding the viscoelastic gel pad to prevent migration due to shoe pressure; and a porous meshwork attached to the elastic retaining ring so as to additionally anchor the gel pad from migration. The porous meshwork member may be located at the surface of the viscoelastic gel pad opposite the aforementioned occlusive covering sheet, or may run through the viscoelastic gel pad in its anchoring function.

Affixing means are provided to secure the viscoelastic gel pad, occlusive covering sheet, and elastic retaining ring with porous meshwork to the digit of the wearer. Possible affixing means include an adhesive tape bandage with a visual access opening, or a transparent digit-engaging elastic tubular sheath.

BRIEF DESCRIPTION OF THE DRAWINGS

FIG. 1 illustrates a perspective view of a human digit to which the medicating device for nails and adjacent tissue has been applied.

FIG. 2 illustrates a top plan view of the medicating device.

FIG. 3 illustrates a cross sectional view of the medicating device, as seen at line 3—3 of FIG. 2, wherein the porous meshwork attached to the perimetric retaining ring is fixed adjacent the viscoelastic gel pad.

FIG. 4 illustrates a cross sectional view of a preferred alternative configuration of the medicating device wherein the porous meshwork attached to the perimetric retaining ring passes through the viscoelastic gel pad.

FIG. 5 illustrates a portion of the lower surface of the viscoelastic gel pad as supported by the porous meshwork, as seen at line 5—5 of FIG. 3.

DETAILED DESCRIPTION OF THE INVENTION

Figure 6:
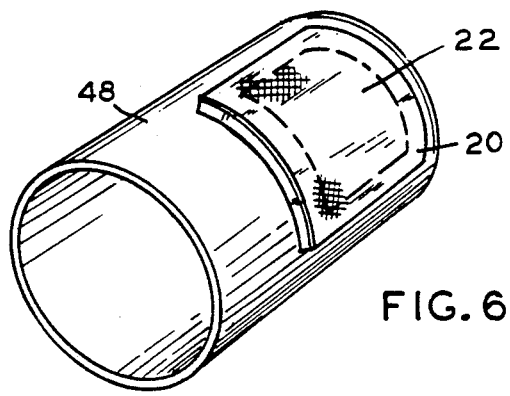
FIG. 6 illustrates a perspective view of the medicating device affixed to an elastic tubular digit-engaging sheath, the sheath being shown inside out.

Turning now to the drawings, there is shown in FIG. 1 the medicating device for human nails and adjacent tissue 10 as applied to the distal end of a human digit 12.

In the preferred embodiment, a viscoelastic gel pad 14, preferably formed in the shape of a trimmed nail 16, is closely surrounded about its lateral perimeter 18 by a flexible elastic retaining ring 20. The retaining ring 20 functions, in conjunction with a porous meshwork 22 discussed subsequently, to prevent migration of the viscoelastic gel pad 14 in response to externally applied pressure such as encountered inside a shoe. The retaining ring 20 preferably is formed in the shape of the viscoelastic gel pad 14 and may be constructed of a soft compressible material such as foam rubber or a noncompressible material such as a silicone compound. Preferably, the retaining ring 20 is made of a soft material that will not inflict pain on the digit 12 of the wearer when external force or pressure is applied. It is also desirable to use a material which is impervious to the liquid fraction of the viscoelastic gel pad 14 in order to prevent evaporation or bleeding of the liquid fraction and subsequent desiccation of the viscoelastic gel pad 14. When a porous material such as foam rubber is used, it is desirable to coat the inside perimetric surface 24 adjacent to the viscoelastic gel pad 14 with a thin layer of impermeable material 26, such as silicone rubber or the like, to prevent desiccation.

The viscoelastic gel pad 14 may utilize a gel having a water, alcohol, or oleaginous liquid fraction. A suitable viscoelastic gel pad 14 has been successfully formed by use of the hydrophilic gel described by King in U.S. Pat. No. 3,419,006. This hydrogel is ninety-six percent water in its fully hydrated state and has a matrix of polyethylene oxide which provides a measure of structural integrity to the viscoelastic gel pad 14. Such viscoelastic gel pad 14 is highly flexible, conforming to the shape of the fungally infected nail and surrounding tissue being treated, so as to apply medication in a prescribed and even manner.

However, the additional use of a porous meshwork 22 has been found to be desirable to provide additional structural integrity in keeping the viscoelastic gel pad 14 intact and preventing the pad 14 from being squeezed out of the retaining ring 20 when repetitive external pressures within a shoe occur. Thus a porous meshwork 22 is affixed to the elastic retaining ring 20 which extends across the central area 28 of the retaining ring 20 so as to support the viscoelastic gel pad 14 within the central area 28. The porous meshwork 22 may be formed of plastic, such as polyethylene oxide, or an elastic material such as rubber which facilitates the stretching of the viscoelastic gel pad 14 in conforming to the contour of the lesion being treated. As seen in FIG. 2, the porous meshwork 22 may be attached, as by adhesive at the lower surface 30 of the retaining ring 20, to extend across the central area 28 adjacent to the lower surface 32 of the viscoelastic gel pad 14. Such a porous meshwork 22 is desirably thin, so as not to provide an impediment to the direct contact of a medicated viscoelastic gel pad 14 against the digit 12 of the wearer. Alternatively, and generally preferable, the porous meshwork 22 may be affixed to extend from the inside perimetric surface 24 of the retaining ring 20 and thus pass within and through the viscoelastic gel pad 14 itself, providing support to the gel pad 14 without the porous meshwork contacting the wearer. Such affixation may occur by the attachment of the porous meshwork 22 within a split 34 within the retaining ring 20, or by joining two sections 36, 38 of a laterally split retaining ring 20 together with said porous meshwork 22 placed therebetween. FIG. 3 illustrates a porous meshwork 22 extending beneath the viscoelastic gel pad 14, while FIG. 4 shows the porous meshwork 22 extending through the pad 14.

The above described viscoelastic gel pad 14 is simple to utilize, wherein, if a hydrogel and initially hydrated, the water may be evaporated off, and then the desiccated pad 14 soaked in the desired aqueous or alcoholic solution to reconstitute the pad with a medication incorporated therein. For example, soaking the desiccated pad in an aqueous solution of urea will result in a gel drug delivery system of value in the nonsurgical avulsion of mycotic nails. Such a urea gel, when incorporated into the present invention, provides a medicator for mycotic nails that is much simplier to use than previous techniques, thus making this mode of treatment much more accessible to health care providers, and even lay persons, than the technically difficult treatment modalities currently employed in this art. In addition to urea, many other medicinal agents can be incorporated into the present invention. For example antifungal agents (fungal agents) such as ciclopirox, chloroxylenol, undecylenic acid, tolnaftate, miconizole, clotrizole, griseofulvin, and ketoconozole may be incorporated into the gel. Antibiotic agents such as mupirocin, erythromycin, gentimycin, neomycin, polymyxin, bacitracin, tetracyclines, and the like may also be incorporated into the gel. Antiseptic agents such as iodine, povidone-iodine, benzalkonium chloride, benzoic acid, chlorhexidine, nitrofurazone, benzoyl peroxide, hexachlorophene, phenol, resorcinol, and cetylpyridinium chloride likewise could be incorporated into the present invention. Furthermore, anti-inflammatories such as hydrocortisone, prednisone, triamcilolone, betamethasone and the like may be incorporated into the gel. Still further, local anesthics such as benzocaine, lidocaine, procaine, bupivicaine, a eutectic mixture of prilocaine and lignocaine, phenol, diphenhydramine, or the like may also be incorporated into the gel. Additional agents that could be incorporated include penetration enhancers such as dimethyl sulfoxide or octolyphenylpolyethelene glycol, keratolytic agents such as salicylic acid, enzymes such as proteases and nucleases, hormones such as insulin, vesicants such as cantharadin, caustics such as podophyllin, and a myriad of additional pharmacologically active substances.

In order to prevent desiccation of the medicated viscoelastic gel pad 14, an impermeable elastic sheet member 40 is attached, as by adhesive, about the upper surface 42 of the retaining ring 20. The sheet member 40 provides an occlusive layer adjacent to the upper surface 44 of the viscoelastic gel pad 14 which prevents evaporation from the upper surface 44 and additionally helps hold the gel pad 14 within the retaining ring 20. The preferred elastic sheet member 40 is transparent, which, with a transparent viscoelastic gel 14, allows the physician and/or wearer to observe the lesion being treated in the placement of the medicating device 10 and in its subsequent monitoring. The porous meshwork 22 may also be transparent, although this is not necessary since the openings 46 in the porous meshwork 22 should be sufficient to allow observation.

Figure 7:
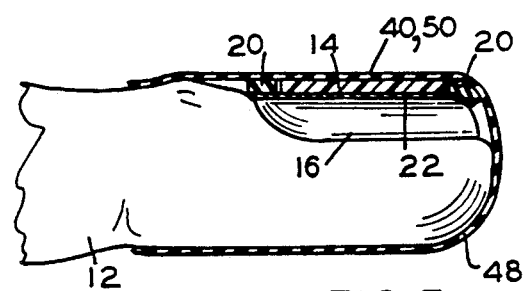
FIG. 7 illustrates a cross sectional view of the medicating device in use, as affixed to the digit-engaging sheath as seen in FIG. 6.

Various means of applying, to a digit 12, the above described medicated viscoelaatic gel pad 14 within the flexible elastic retaining ring 20 with affixed porous meshwork 22, in either of the forms shown in FIGS. 3 and 4, may be used. A preferred means includes, as illustrated in FIGS. 6 and 7, an impermeable elastic tubular digit encasing sheath 48 to which the retaining ring 20 is affixed. FIG. 6 shows the sheath 48 in an inside out position, which allows the sheath 48 to be applied by rolling over the end of the digit 12 to an applied position as seen at FIG. 7. Use of the sheath 48 allows a portion 50 of the sheath 48, located within the central area 28 of the retaining ring 20, to be utilized in place of the sheet member 40. The sheath 48, in a form similar to a finger cut from a latex surgeon's glove, is easily applied over the end of the digit 12 and holds the viscoelastic gel pad 14 and retaining ring 20 in place upon the offending digit 12. The preferred sheath 48 is transparent, such transparency not only allowing observation of the medicated viscoelastic gel pad 14 during and after application, but also allows observation of the circulation status of the treated digit 12.

Figure 8:
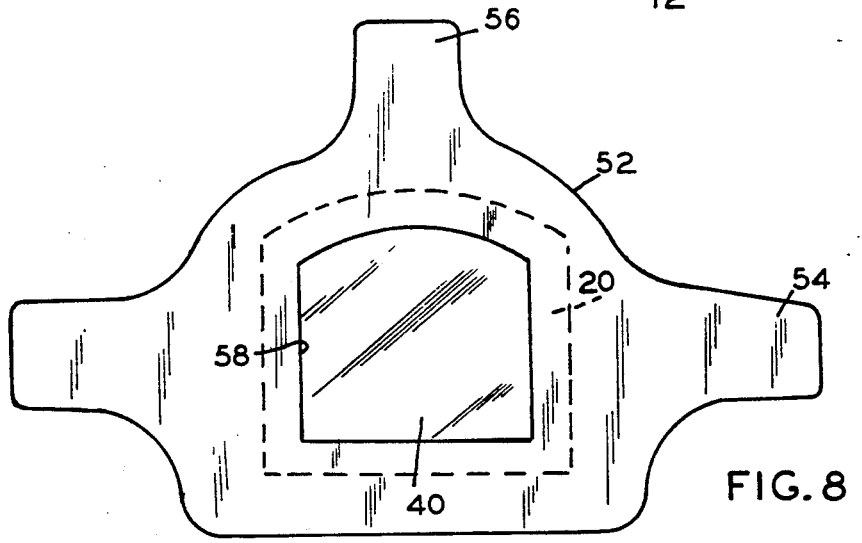
FIG. 8 illustrates a top plan view of the medicating device affixed to an adhesive tape bandage designed for digit application.
Figure 9:
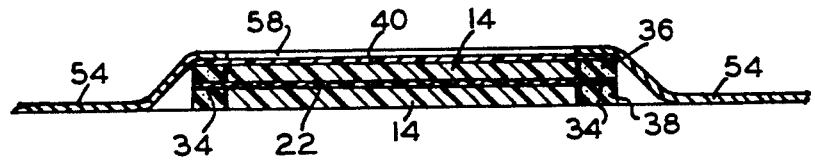
FIG. 9 illustrates a cross sectional view of the medicating device with adhesive tape bandage.

An alternative means for applying the viscoelastic gel pad 14 and retaining ring 20 is by the use of an adhesive bandage 52. As illustrated in FIGS. 8 and 9, such an adhesive bandage 52 may have opposing digit encircling flaps 54, and a distally extending flap 56 which engages the distal and plantar or palmar surfaces of the digit 12. The adhesive bandage preferably includes an opening or window 58 through which observation may occur. The bandage 52 is attached at the upper surface 42 of the retaining ring 20, along with the sheet member 40. The preferred adhesive bandage 52 is itself waterproof to permit bathing without disrupting the medicating device 10.

It is thought that the medicating device 10 for nails and adjacent tissue of the present invention and its many attendant advantages will be understood from the foregoing description and that it will be apparent that various changes in form, construction and arrangement of the parts thereof may be made without departing from the spirit and scope of the invention or sacrificing all of its material advantages, the form hereinbefore described being merely an exemplary embodiment thereof.

I claim:

1. A medicating device for human nails and adjacent tissue comprising:
    a. a viscoelastic gel pad, having an upper surface, a lower surface, and a lateral perimeter;
    b. a flexible, elastic retaining ring formed to fit closely about the lateral perimeter of said viscoelastic gel pad; said retaining ring having an upper surface and a lower surface, and bounding a central area wherein said viscoelastic gel pad is located;
    c. an impermeable, elastic sheet member, attached about the upper surface of said retaining ring, which provides an occlusive layer adjacent to said upper surface of said viscoelastic gel pad;
    d. a thin, porous meshwork affixed to said retaining ring and extending across said central area of said retaining ring to support said viscoelastic gel pad within said central area; and
    e. means for attaching said viscoelastic gel pad and said flexible elastic retaining ring with affixed porous meshwork to a digit of a wearer.

2. The medicating device for human nails and adjacent tissue, as recited in claim 1, wherein said thin, porous meshwork is positioned adjacent to said lower surface of said viscelastic gel pad.

3. The medicating device for human nails and adjacent tissue, as recited in claim 1, wherein said thin, porous meshwork is positioned within and extends through said viscoelastic gel pad.

4. The medicating device for human nails and adjacent tissue, as recited in claim 1, wherein said means for affixing said medicating device for human nails and adjacent tissue to a digit of a wearer includes an adhesive bandage.

5. The medicating device for human nails and adjacent tissue, as recited in claim 4, wherein said adhesive bandage includes a window adjacent said impermeable elastic sheet member.

6. The medicating device for human nails and adjacent tissue, as recited in claim 1, wherein said means for affixing said medicating device for human nails and adjacent tissue to a digit of a wearer includes an elastic tubular digit-encasing sheath.

7. The medicating device for human nails and adjacent tissue, as recited in claim 6, wherein a portion of said elastic tubular digit-encasing sheath, located adjacent to said upper surface of said viscoelastic gel pad, is utilized as said impermeable, elastic sheet member.

8. The medicating device for human nails and adjacent tissue, as recited in claim 1, wherein said viscoelastic gel pad and impermeable, elastic sheet member are transparent.

9. The medicating device for human nails and adjacent tissue, as recited in claim 1, wherein said viscoelastic gel pad is perfused with one or more pharmacologically active agents.

10. The medicating device for human nails and adjacent tissue, as recited in claim 9, wherein said pharmacologically active agents are urea, antifungal agents, antibiotics, keratolytic agents, local anesthetics, alcohols, or proteolytic enzymes

* * * * *